(12) United States Patent
Ditzel et al.

(10) Patent No.: US 8,471,058 B2
(45) Date of Patent: Jun. 25, 2013

(54) CARBONYLATION PROCESS USING BOUND SILVER AND/OR COPPER MORDENITE CATALYSTS

(75) Inventors: Evert Jan Ditzel, Goole (GB); David John Law, Beverley (GB); John Glenn Sunley, Cottingham (GB)

(73) Assignee: BP Chemicals Limited, Middlesex (GB)

( * ) Notice: Subject to any disclaimer, the term of this patent is extended or adjusted under 35 U.S.C. 154(b) by 0 days.

(21) Appl. No.: 12/998,845

(22) PCT Filed: Nov. 16, 2009

(86) PCT No.: PCT/GB2009/002673
§ 371 (c)(1),
(2), (4) Date: Jun. 8, 2011

(87) PCT Pub. No.: WO2010/067043
PCT Pub. Date: Jun. 17, 2010

(65) Prior Publication Data
US 2011/0237825 A1   Sep. 29, 2011

(30) Foreign Application Priority Data
Dec. 10, 2008   (EP) .................................... 08253942

(51) Int. Cl.
*C07C 67/36*   (2006.01)
*C07C 51/12*   (2006.01)
*C07C 67/37*   (2006.01)

(52) U.S. Cl.
CPC ................. *C07C 51/12* (2013.01); *C07C 67/37* (2013.01)

USPC ........................................... 560/232; 562/519

(58) Field of Classification Search
CPC ................................. C07C 51/12; C07C 67/37
See application file for complete search history.

(56) References Cited

U.S. PATENT DOCUMENTS
2006/0052236 A1 *   3/2006   Angevine et al. ............... 502/66

OTHER PUBLICATIONS

Ellis et al, Studies in Surface Science and Catalysis, Heterogeneous Catalysts for the Direct, Halide-free Carbonylation of Methanol, 1996, 101, pp. 771-779.*
International Search Report for PCT/GB2009/00002673, mailed Mar. 31, 2010.
Written Opinion of the International Searching Authority for PCT/GB2009/00002673, mailed Mar. 31, 2010.
International Preliminary Report on Patentability for PCT/GB2009/002673, dated Sep. 15, 2010.

* cited by examiner

*Primary Examiner* — Paul A Zucker
(74) *Attorney, Agent, or Firm* — Nixon & Vanderhye

(57) ABSTRACT

Process for the carbonylation of a carbonylatable reactant selected from at least one of dimethyl ether and methanol, by carbonylating the carbonylatable reactant with carbon monoxide in the presence of a catalyst to produce a carbonylation product selected from at least one of methyl acetate and acetic acid. The catalyst is formed by compositing a mordenite loaded with at least one of silver and copper, with an inorganic oxide binder.

14 Claims, 2 Drawing Sheets

CARBONYLATION PROCESS USING BOUND SILVER AND/OR COPPER MORDENITE CATALYSTS

This application is the U.S. national phase of International Application No. PCT/GB2009/002673, filed 16 Nov. 2009, which designated the U.S., and claims priority to EP Application No. 08253942.0, filed 10 Dec. 2008, the entire contents of each of which are hereby incorporated by reference.

BACKGROUND OF THE INVENTION

This invention relates to a method of preparing metal loaded bound mordenite zeolites and their use as carbonylation catalysts.

Bound mordenites have been demonstrated to be suitable for use as catalysts in hydrocarbon conversion processes such as the transalkylation of aromatic hydrocarbons, as described in U.S. Pat. No. 6,486,372 and the hydrocracking of high boiling hydrocarbon feedstocks, as described in WO 97/13826.

SUMMARY OF THE INVENTION

Mordenite has also been disclosed as a catalyst in gas phase carbonylation processes employing dimethyl ether as carbonylatable reactant. For example, there is described in WO 2006/121778 a process for the production of a lower alkyl ester of a lower aliphatic carboxylic acid by carbonylating under substantially anhydrous conditions a lower alkyl ether, such as dimethyl ether, with carbon monoxide in the presence of a mordenite or ferrierite catalyst. There is no disclosure in WO 2006/121778 of the use of a bound mordenite zeolite in the carbonylation process.

In EP-A-2000433 there is described a process for the production of acetic acid and/or methyl acetate by contacting methanol and/or a reactive derivative thereof with a decomposition catalyst to produce a mixture of carbon monoxide and hydrogen and subsequently catalytically converting the carbon monoxide and hydrogen to acetic acid and/or methyl acetate. Mordenites are disclosed as suitable catalysts for the conversion of the mixture of carbon monoxide and hydrogen to acetic acid and/or methyl acetate.

WO 2007/128955 discloses a process for preparing a carboxylic acid and/or ester thereof by carbonylating an alcohol and/or reactive derivative thereof with carbon monoxide in the presence of a silver loaded mordenite catalyst.

In an article entitled 'Heterogeneous Catalysts for the Direct, Halide-free Carbonylation of Methanol' by Ellis B et al, 11th International Congress on Catalysis—40th Anniversary, Studies in Surface Science and Catalysis, Vol. 101, pages 771-779, 1996, there is disclosed the use of copper loaded mordenites as catalysts for the heterogeneous carbonylation of methanol.

It is known, for example, from the afore-mentioned WO 2007/128955 that metal loaded mordenites can be used to catalyse the carbonylation of methanol. To facilitate the handling and compression strength of zeolite catalysts, zeolites are typically combined with a binder material and formed into beads, pellets or extrudates. However, a disadvantage to the use of binders is that because they are considered to be inert, efforts are made to minimise the amount of binder used as it replaces the active catalyst component. Thus, for equivalent volumes of a catalyst with binder and a catalyst without a binder, the former is likely to show the greater catalytic activity. It would therefore be desirable to provide a metal loaded mordenite which is composited with a binder but wherein there is no substantial reduction in catalytic activity.

It has now been found that in carbonylation processes, this can be achieved if the mordenite is loaded with copper and/or silver prior to being composited with the binder. Surprisingly, catalysts which are prepared by forming a composite of mordenite with binder and then subsequently loaded with copper and/or silver have been found to be inferior catalysts.

Accordingly, the present invention provides a process for the carbonylation of a carbonylatable reactant selected from at least one of dimethyl ether and methanol, with carbon monoxide in the presence of a catalyst to produce a carbonylation product selected from at least one of methyl acetate and acetic acid, which catalyst is formed by compositing a mordenite loaded with at least one of silver and copper, with an inorganic oxide binder.

The catalyst for use in the present invention is a mordenite loaded with at least one of copper and silver and composited with an inorganic oxide binder.

Mordenite is a zeolite and its structure is well known and is defined, for example, in The *Atlas of Zeolite Framework Types* (C. Baerlocher, W. M. Meier, D. H. Olson, 5$^{th}$ ed. Elsevier, Amsterdam, 2001). The web-based version (http://www.iza-structure.org/databases/) is a compendium of topological and structural details about zeolites including mordenite.

Mordenite can be obtained commercially or it may be synthesised. Commercially available forms of mordenite include the sodium form, the acid form and the ammonium form. The preferred form of mordenite for use in the present invention is the acid form (H-form) of mordenite. The sodium and ammonium forms can be converted to the acid form of mordenite by well-known techniques. For example, the ammonium form can be converted to the acid form by calcining the ammonium form at high temperature. The sodium form can be converted to the acid form by converting first to the ammonium form by ion exchange with ammonium salts such as ammonium nitrate and then calcining the ammonium form at high temperature.

Typically, mordenite has a silica:alumina ratio in the range 10 to 100:1 and such mordenites are suitable for use in the present invention. Preferably, however, the silica:alumina ratio of the mordenite for use in the present invention is in the range 10 to 40:1

Preferably, the Brunauer-Emmett-Teller (BET) surface area of the mordenite is in the range 100 to 500 m$^2$/g as measured by nitrogen absorption. The measurement of BET surface area is described by Charles N. Satterfield in Heterogeneous Catalysis in Practice, McGraw-Hill Book company, 1980 p. 100-106.

In the present invention, mordenite is loaded with one or more of copper and silver. The loading of copper and/or silver metal onto mordenite may be achieved by any process known to the skilled person, such as by the techniques of wet impregnation, incipient wetness and ion-exchange. Where ion-exchange is used, up to 100% of the cation-exchangeable sites on the mordenite may be exchanged with copper and/or silver metal ions. It is preferred that any remaining cations in the exchanged mordenite are protons hence it is convenient to start the exchange process from the ammonium or acid form of mordenite.

As an alternative to ion-exchange, the ammonium or acid form of mordenite can be impregnated with a solution of a copper and/or silver salt and subsequently dried.

Preferably, the loading of the metal(s) onto mordenite is carried out by ion-exchange.

The following ion-exchange method may be employed to prepare a copper and/or silver loaded mordenite. Mordenite in a suitable form, such as H-mordenite or $NH_4$-mordenite, is contacted with an aqueous solution of a metal salt selected from a copper (I) or (II) salt, a silver (I) salt.

Suitable copper (I) salts include copper halides, such as copper chloride, and copper acetate.

Suitable copper (II) salts include copper nitrate, copper acetate, copper sulphate, copper oxalates, copper halides such as copper chloride.

Suitable silver (I) salts include silver nitrate, silver acetate, silver triflate.

In the presence of white light silver salts tend to undergo light promoted reduction to silver metal so it is preferred that the ion-exchange is carried out in the substantial absence of light.

The metal salt is used in the form of an aqueous solution by dissolving the salt in any suitable solvent. Suitable solvents include deionised water and a solution of ammonium hydroxide in deionised water.

The mordenite is contacted with the metal salt solution such that the mordenite is at or above its level of incipient wetness.

Optionally, the mordenite/aqueous solution mixture may be heated provided that the level of incipient wetness is maintained and the residual metal salt solution remains as a solution. At atmospheric pressure, a suitable temperature may be in the range 60 to 90° C. The solution may be heated until the desired level of metal loading is reached.

The optionally heated solution is then filtered to remove excess metal salt solution and to recover a solid metal loaded mordenite.

After filtering, the solid metal loaded mordenite is washed with a solvent in which the metal salt solution is soluble and which solvent does not remove the exchanged metal from the mordenite. Suitable solvents include deionised water.

Preferably, the washed metal loaded mordenite is then dried to remove residual water to achieve a free-flowing powder. Preferably, drying is carried out by heating the metal loaded mordenite to a temperature of at least 90° C., for example 90 to 120° C. The heating may be conducted in static or free-flowing air or in an inert gas such as nitrogen.

Prior to use in a carbonylation reaction, the metal loaded mordenite may be calcined at a temperature in the range 400 to 600° C. The calcination may be carried out in static or free-flowing air or in an inert gas such as nitrogen.

The amount of copper and/or silver metal loaded onto the mordenite can be expressed in terms of the fractional loading of the metal as gram atoms of metal per gram atom of aluminium in the mordenite. The metal loading can also be expressed as a mole percentage loading relative to aluminium in the mordenite through the relationship:

$$\text{mol \% Metal} = (\text{gram atoms Metal/gram atoms aluminium}) \times 100$$

Thus, for example, a loading of 0.55 gram atom of copper per aluminium in the mordenite equates to a 55 mol % loading of copper relative to aluminium in the mordenite.

For use in the present invention, the degree of metal loading is not critical but is preferably in the range 5 to 200 mol % relative to aluminium in the mordenite.

In the present invention, the copper and/or silver is loaded onto the mordenite prior to mixing the loaded mordenite with an inorganic oxide binder.

Inorganic oxides which are suitable as binders for use in the present invention include silicas, aluminas, silica-aluminas, magnesium silicates, magnesium aluminium silicates, titanias, zirconias and clays. For use in the present invention, alumina or silica-alumina binders are particularly useful. Examples of suitable aluminas include boehmite type alumina and gamma alumina. Where a silica-alumina is used, the silicate content is preferably in the range 5 to 40 wt %. The silica-alumina is preferably also amorphous.

It is preferred that the binder is not a zeolite.

Preferably, the binder is a refractory inorganic oxide such that the binder is stable at high temperature, and, in particular is stable at temperatures which may be employed in calcination of the catalyst, such as a temperature of at least 400° C.

Preferably, the binder is mesoporous. For the purposes of this invention, a mesopore is a pore having a diameter in the range of 2 to 50 nanometers and the expression 'mesoporosity' means the sum of the total surface area of the mesopores and the external surface area of the inorganic oxide binder material as measured by nitrogen BET. Suitably, the mesoporosity of the binder is in the range 1 to 500 $m^2/g$.

Preferably, the binder has a low microporosity. For the purposes of this invention a micropore is a pore having a diameter of less than 2 nanometers and the expression 'microporosity' means the total surface area of the micropores of the inorganic oxide binder material as measured by nitrogen BET. Suitably, the microporosity of the binder is in the range 1 to 100 $m^2/g$, such as in the range 1 to 10 $m^2/g$.

Suitably, the binder is present in an amount in the range of 10% to 80% by weight of the catalyst, preferably, in the range of 20% to 60% by weight of the catalyst or in the range 20 to 65% by weight of the catalyst, such as 35 to 65% by weight of catalyst.

It has been found that binders which contain low levels of metallic impurities such as iron and metals of Group 1 and Group 2 of the Periodic Table of Elements, for example, sodium, potassium, calcium and magnesium, are particularly useful in the present invention. Thus, preferably, the total amount of metallic impurities in the binder is in the range greater than 0 to 10 wt % and, more preferably, in the range greater than 0 to 7 wt %.

The catalyst for use in the present invention is prepared by forming an intimate mixture (a composite) of the inorganic oxide binder and the copper and/or silver loaded mordenite. An intimate mixture of the binder and the metal loaded mordenite may be prepared, for example, by slurry mixing, dry mixing, shear mixing or tumble mixing of the binder and metal loaded mordenite components to produce a uniform dispersion of the two components with one another. After mixing, the bound metal loaded mordenite may be, and is, preferably, calcined. In general, calcination is carried out at a temperature in the range 400 to 500° C. Prior to use, the calcined catalyst may be pressed, crushed and sieved to form aggregates.

One method for preparing the catalyst consists of slurry mixing the metal loaded mordenite with the binder. In slurry mixing, the mordenite, binder and deionised water are mixed, for a period necessary to obtain a wet homogeneous paste or slurry. The slurry is then dried, for example, at a temperature in the range 80 to 120° C. for several hours to remove any excess water and all or substantially all of the physi-sorbed water. The drying may be carried out either at atmospheric pressure or under reduced pressure. Optionally, prior to drying of the wet paste or slurry, it may be shaped by pressing, extruding or granulating to produce pellets, extrudates or beads. The dried slurry or shaped form of the slurry may then be calcined at a temperature in the range 400 to 500° C. for a period of from about 1 to 10 hours to form the catalyst.

Alternatively, the catalyst may be formed by intimately mixing a metal loaded mordenite in powder form with a dry binder to form a composite of the metal loaded mordenite and binder. The dry mixing may be carried out by any suitable mechanism, such as by tumbling or rotation. The composite may then be calcined. Calcination may be carried out a temperature in the range 400 to 500° C. for a period of from about 1 to 10 hours to form the catalyst.

The composites formed by combining copper and/or silver loaded mordenites with an inorganic oxide binder have been found to possess improved catalytic performance in the carbonylation of dimethyl ether and/or methanol to produce methyl acetate and/or acetic acid, compared to mordenite/binder composites onto which is loaded copper and/or silver.

The carbonylatable reactant may be dimethyl ether, methanol or mixtures thereof.

Where the carbonylatable reactant is dimethyl ether, it may be substantially pure or may contain low levels of inert impurities. In commercial practice, dimethyl ether is produced by the catalytic conversion of synthesis gas (mixtures of hydrogen and carbon monoxide) over methanol synthesis and methanol dehydration catalysts. This catalytic conversion results in a product which is predominantly dimethyl ether but it may also contain some methanol. For use in the process of the present invention the dimethyl ether feed may comprise small amounts of methanol provided that the amount of methanol present in the feed is not so great as to inhibit the carbonylation of dimethyl ether to methyl acetate product. It has been found that 5 wt % or less, such as 1 wt % or less of methanol may be tolerated in the dimethyl ether feed.

Alternatively, dimethyl ether may be generated in-situ from any suitable source, such as dimethyl carbonate. For example, liquid dimethyl carbonate may be contacted with gamma-alumina to decompose the dimethyl carbonate to dimethyl ether and carbon dioxide.

Suitably, the concentration of dimethyl ether in the gaseous feed is in the range of 0.1 to 20 mol %, based on the total gaseous feed (including recycles).

The carbon monoxide may be substantially pure carbon monoxide, for example, carbon monoxide typically provided by suppliers of industrial gases, or it may contain impurities that do not interfere with the conversion of the carbonylatable reactant to the carbonylation product, such as nitrogen, helium, argon, methane and/or carbon dioxide.

The carbonylation process may be conducted in the presence of hydrogen. Thus, the carbon monoxide feed may also contain hydrogen. Mixtures of hydrogen and carbon monoxide are commercially produced by the steam reforming of hydrocarbons and by the partial oxidation of hydrocarbons. Such mixtures are commonly referred to as synthesis gas. Synthesis gas comprises mainly carbon monoxide and hydrogen but may also contain smaller quantities of carbon dioxide.

Suitably, the molar ratio of carbon monoxide:hydrogen may be in the range 1:3 to 15:1, such as 1:1 to 10:1.

Where hydrogen is present in the process, it may be present at a partial pressure of at least 0.1 barg, such as 1 to 30 barg.

The molar ratio of carbon monoxide to carbonylatable reactant is suitably in the range 1:1 to 99:1, such as 2:1 to 60:1.

Where the carbonylatable reactant is methanol, water is generated in-situ by the dimerisation of the methanol to ethers or via esterification of the methanol with acetic acid product. If desired, water may be added to the methanol feed. The amount of water added may be such that the molar ratio of methanol:water is in the range 50:1 to 2:1. The water may be fed separately to or together with the methanol feed. The water may be fed either as a liquid or as a vapour.

The carbonylation of dimethyl ether to methyl acetate does not generate water in-situ. As water has been found to inhibit the carbonylation of dimethyl ether to form methyl acetate, it is preferred that the carbonylation of dimethyl ether is carried out as an anhydrous process. Thus, water is kept as low as is feasible. To accomplish this, the dimethyl ether, carbon monoxide, optional hydrogen and catalyst are preferably dried prior to use. However, small amounts of water may be tolerated in the process without adversely affecting the formation of methyl acetate. Suitably, water may be present in the dimethyl ether feed in an amount of 2.5 wt % or less, such as 0.5 wt % or less.

The process may suitably be carried out at a temperature in the range of 100° C. to 400° C., such as 150 to 350° C.

The process may be carried out at a pressure in the range 1 to 100 barg, such as 10 to 100 barg.

The Gas Hourly Space Velocity (GHSV) is suitably in the range 500 to 40,000 $h^{-1}$, such as 4000 to 10,000 $h^{-1}$.

It is preferred that the catalyst is activated immediately before use by heating the catalyst at elevated temperature for at least one hour under flowing nitrogen, carbon monoxide, hydrogen or mixtures thereof.

Preferably, the process is carried out substantially in the absence of halides, such as iodide. By the term 'substantially' is meant that the total halide, for example, iodide content of the reactant gases (carbonylatable reactant and carbon monoxide) and catalyst is less than 500 ppm, preferably less than 100 ppm.

The process is suitably carried out by passing carbonylatable reactant vapour, carbon monoxide gas and, optional hydrogen gas, through a fixed bed, fluidised bed or moving bed of the catalyst maintained at the desired temperature and pressure.

If desired, the carbonylatable reactant may be contacted with a bed of alumina or corundum immediately prior to the bed of catalyst.

Where the carbonylatable reactant is methanol, the predominant carbonylation product will be acetic acid but small amounts of methyl acetate may also be produced, depending on the degree of conversion of methanol.

Where the carbonylatable reactant is dimethyl ether, the primary product of the process is methyl acetate but small amounts of acetic acid may also be produced.

The products of the process of the present invention are methyl acetate and/or acetic acid. Where the carbonylatable reactant is methanol, the predominant carbonylation product will be acetic acid but small amounts of methyl acetate may also be produced, depending on the degree of conversion of methanol. Where the carbonylatable reactant is dimethyl ether, the primary product of the process is methyl acetate but small amounts of acetic acid may also be produced. The acetic acid and/or methyl acetate produced by the process of the present invention can be removed in the form of a vapour and thereafter condensed to a liquid.

In addition to acetic acid and methyl acetate, the product stream from the process of the present invention may also comprise, unconverted dimethyl ether and/or unconverted methanol.

Methyl acetate and/or acetic acid may be recovered from the product stream by conventional techniques such as distillation.

The methyl acetate may be sold as such or it may be forwarded to other chemical processes. For example, at least part of the methyl acetate product may be hydrolysed to acetic acid.

Alternatively, at least part of the entire product stream of the present process, and which comprises methyl acetate, may be passed to a hydrolysis stage from which acetic acid is subsequently separated therefrom.

Hydrolysis of methyl acetate may be carried out by known techniques such as reactive distillation in the presence of an acid catalyst.

Acetic acid which is recovered from the product stream of the present invention or which is subsequently produced by hydrolysis of methyl acetate can be purified using conventional purification techniques, such as distillation.

The process may be operated as either a continuous or a batch process, preferably as a continuous process.

BRIEF DESCRIPTION OF THE DRAWINGS

In the Figures.

Figure 1:
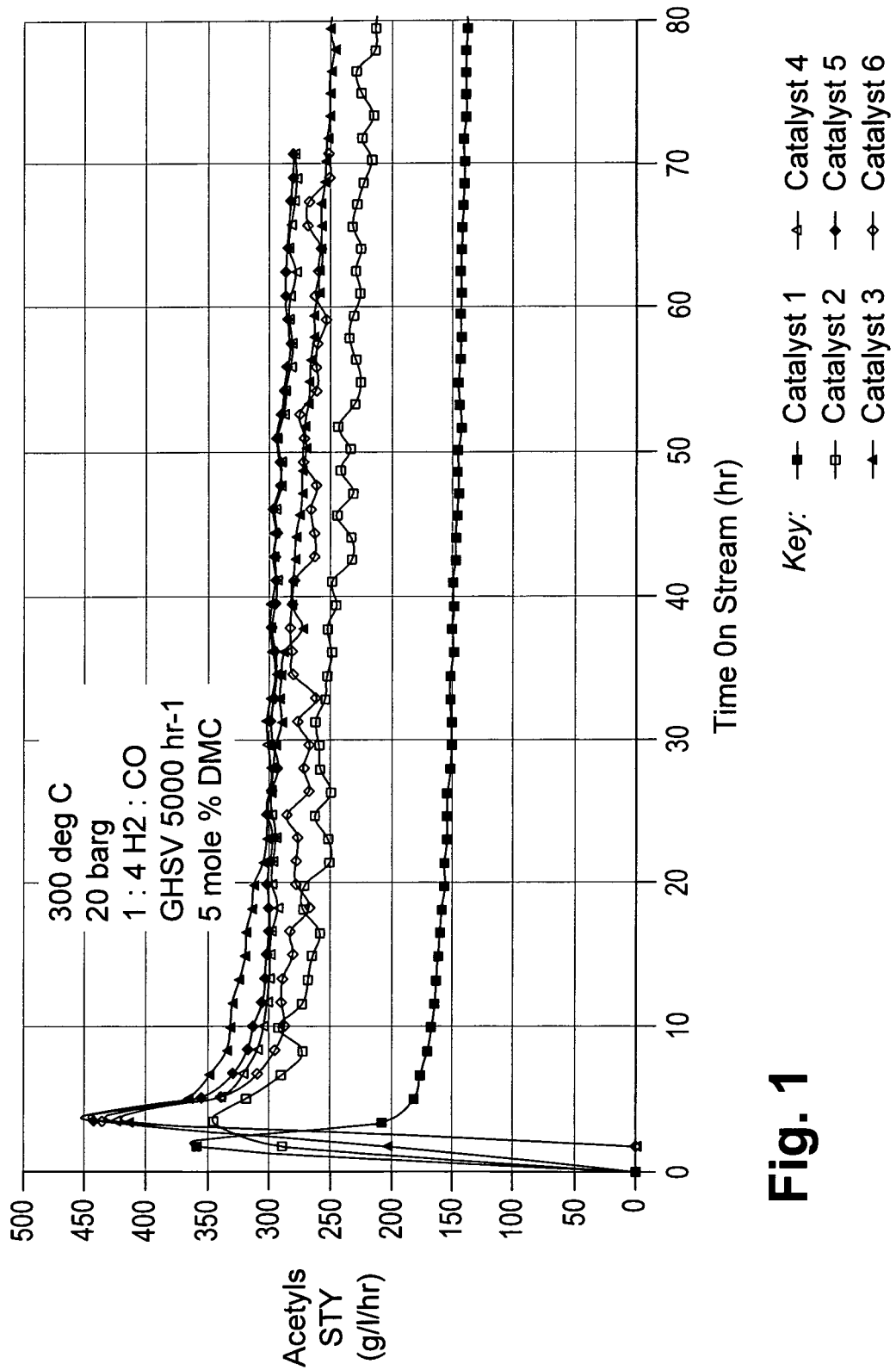
FIG. 1 depicts space time yield (STY) to carbonylation products (g/l/h) versus time on stream (hours) for various composites of copper mordenite with Pural SB binder.

The invention is now illustrated with reference to the following Examples.

EXAMPLE 1

This Example demonstrates the effect on the carbonylation of dimethyl ether of catalysts prepared by combining copper mordenite with an inorganic oxide binder (Catalysts 3 to 6) compared to catalysts prepared by mixing mordenite with a binder to form a bound mordenite and subsequently loading copper onto the bound mordenite (Catalysts 1 and 2). Pural SB (a boehmite alumina, Sasol) was used as the binder in the preparation of Catalysts 1 to 6. Pural SB has a mesoporosity of 274 $m^2/g$, a microporosity of <10 $m^2/g$ and 0.19 wt % in total of Na, K, Ca, Mg and Fe metal impurities.

Each of Catalysts 1 to 6 had a copper loading of 55 mol % relative to aluminium in the mordenite and the weight ratio of each catalyst:binder was 80:20.

Preparation of Catalyst 1 (not in Accordance with the Invention)

8 g of $NH_4$-mordenite with a silica to alumina ratio of 20 (CBV21A ex Zeolyst) was mixed with 2 g of Pural SB binder. Deionised water was added to the mixture to obtain a thick slurry and stirred thoroughly. The slurry mixture was then dried at 110° C. for at least 20 hours. The dried mixture together with 1.48 g of copper (II) nitrate hemipentahydrate (98% ACS) were placed into a 100 mL round bottomed flask equipped with a stirrer. 25 ml deionised water was added to the mixture to obtain a mobile slurry. The top of the flask was loosely covered and the contents were stirred overnight. The stirred mobile slurry was then dried under reduced vacuum using a rotary evaporator before being dried in an oven at 110° C. for at least 15 hours to obtain a dry catalyst, Catalyst 1. Catalyst 1 was then calcined in accordance with the calcination method described below.

Preparation of Catalyst 2 (not in Accordance with the Invention)

The preparation of Catalyst 1 was repeated except that 4.5 ml deionised water (to reach the point of incipient wetness) was added to the dried binder/mordenite mixture and the 1.48 g of copper (II) nitrate hemipentahydrate (98% ACS). This mixture was then agitated vigorously for 15 minutes to enable uniform mixing before being dried in accordance with the procedure described in the preparation of Catalyst 1. The dry catalyst was then calcined using the calcination method described below.

Preparation of Copper Mordenite (for Use in the Preparation of Catalysts 3 to 6)

40 g $NH_4$-mordenite of silica:alumina ratio of 20 (CBV21A, Zeolyst) and 7.4 g of copper (II) nitrate hemipentahydrate (98% ACS) were placed into a 500 mL round bottomed flask equipped with a stirrer. 100 ml deionised water was added to obtain a mobile slurry. The top of the flask was loosely covered and left to stir overnight. The mobile slurry was then dried under reduced vacuum using a rotary evaporator before being dried in an oven at 110° C. for at least 15 hours to obtain a dry copper mordenite catalyst. The catalyst had a copper loading of 55 mol % relative to aluminium in the mordenite Preparation of Catalyst 3

8 g of dry copper mordenite (prepared as described above) was mixed with 2 g of Pural SB binder. Deionised water was added to the mixture to obtain a thick slurry and stirred thoroughly. The slurry was then dried in an oven at 110° C. for at least 20 hours to obtain a dry catalyst. The dry catalyst was then calcined in accordance with the calcination method described below.

Preparation of Catalyst 4

Copper mordenite (prepared as described above) was calcined in accordance with the calcination method described below to prepare a calcined copper mordenite. The preparation method for Catalyst 3 was then repeated using 8 g of the calcined copper mordenite so prepared.

Preparation of Catalyst 5

8 g of dry copper mordenite (prepared as described above) was milled to obtain a free flowing powder. The powder and 1 g of Pural SB binder were added to a 500 ml Buchi powder drying flask and rotated at 100 rpm at ambient temperature and pressure for 1 hour to obtain a catalyst of copper mordenite composited with Pural SB binder. The catalyst was then calcined using the calcination method described below.

Preparation of Catalyst 6

Copper mordenite (prepared as described above) was calcined in accordance with the calcination method described below to prepare a calcined copper mordenite. The preparation method for Catalyst 5 was then repeated using 8 g of the calcined copper mordenite so prepared.

Calcination Method

Calcination of a catalyst was carried out in an oven under a static atmosphere of air by increasing the temperature from room temperature to 90° C. at a ramp rate of 3° C./min. and held at this temperature for 2 hours. The temperature was then increased to 110° C. at a ramp rate of about 0.6° C./min and held at this temperature for 2 hours. Finally, the temperature was increased to 500° C. at a ramp rate of about 3.3° C./min and held at this temperature for 3 hours before being allowed to cool to room temperature.

Carbonylation of Dimethyl Ether

Each of the Catalysts 1 to 6 was used to carbonylate dimethyl ether in accordance with the following procedure. Prior to use in a carbonylation reaction each catalyst was compacted at 12 tonnes in a 33 mm die set using a Specac Press, and then crushed and sieved to a pellet size fraction of 250 to 500 microns.

The carbonylation reactions were carried out on a pressure flow reactor unit comprising 16 reactors. A Hastelloy reactor tube with an integral electrical heating jacket was packed with 0.6 ml of a catalyst and 0.2 g of a gamma alumina pre-bed. The reactor and heating jacket were installed on the unit in a heated cabinet. The temperature of the catalyst bed was controlled by the integral heating jacket and the temperature of the pre-bed was controlled by the heated cabinet. The reactor was heated at atmospheric pressure under a flow of nitrogen to 130° C. in the heated cabinet and maintained at this temperature. The feed gas was then changed to 80 mol % carbon monoxide and 20 mol % hydrogen and the system was pressurised to 20 barg. The gas flow rate (GHSV) for these and all subsequent steps was 5000 hr$^{-1}$. During this time the reactor was heated to 300° C. at a ramp rate of 3° C. per minute using the electrical heating jacket and the system was then held under these conditions for two hours. The carbonylation reaction was then started by feeding dimethyl carbonate at a rate designed to give a gas feed comprising 76 mole % carbon monoxide, 19 mole % hydrogen and 5 mole % dimethyl ether. A constant flow of reaction off-gases was taken from the high pressure side of the reactor system through a needle valve, let down to atmospheric pressure at a temperature of at least 130° C. and passed to a gas chromatograph for analysis of the carbonylation acetyls products (methyl acetate and acetic acid). The results of the carbonylation reactions are shown in FIG. 1.

As can be seen from FIG. 1, Catalysts 3 to 6 provide improved STY to carbonylation products compared to Catalysts 1 and 2 which were not prepared in accordance with the invention.

EXAMPLE 2

This Example demonstrates the effect on the carbonylation of dimethyl ether of catalysts prepared by combining copper mordenite with a binder (Catalysts 9 and 10); catalysts prepared by mixing mordenite with a binder to form a bound mordenite and subsequently loading the bound mordenite with copper (Catalysts 7 and 8); and a copper mordenite catalyst having no binder (Catalyst 11).

Chinafill 200 (an aluminosilicate clay, Amberge Kaolinwerke) was used as the binder in the preparation of each of Catalysts 7 to 10. Chinafill 200 has a mesoporosity of <10 m$^2$/g, a microporosity of <10 m$^2$/g and 2.94 wt % in total of Na, K, Ca, Mg and Fe metal impurities.

Each of Catalysts 9 to 11 had a copper loading of 55 mol % relative to aluminium in the mordenite and the weight ratio of each catalyst:binder was 80:20.
Preparation of Catalyst 7 (not in Accordance with the Invention)
The preparation of Catalyst 1 was repeated except that Chinafill 200 was used as the binder instead of Pural SB.
Preparation of Catalyst 8 (not in Accordance with the Invention)
The preparation of Catalyst 2 was repeated except that Chinafill 200 was used as the binder instead of Pural SB.
Preparation of Catalyst 9
The preparation of Catalyst 3 was repeated except that Chinafill 200 was used as the binder instead of Pural SB.
Preparation of Catalyst 10
The preparation of Catalyst 5 was repeated except that Chinafill 200 was used as the binder instead of Pural SB.
Preparation of Catalyst 11 (not in Accordance with the Invention)
Copper mordenite was prepared as described above and then calcined in accordance with the calcination method described above. No binder was used in the preparation of this catalyst.
Carbonylation of Dimethyl Ether
Each of the Catalysts 7 to 11 was used to carbonylate dimethyl ether in accordance with carbonylation reaction method described in Example 1.

Figure 2:
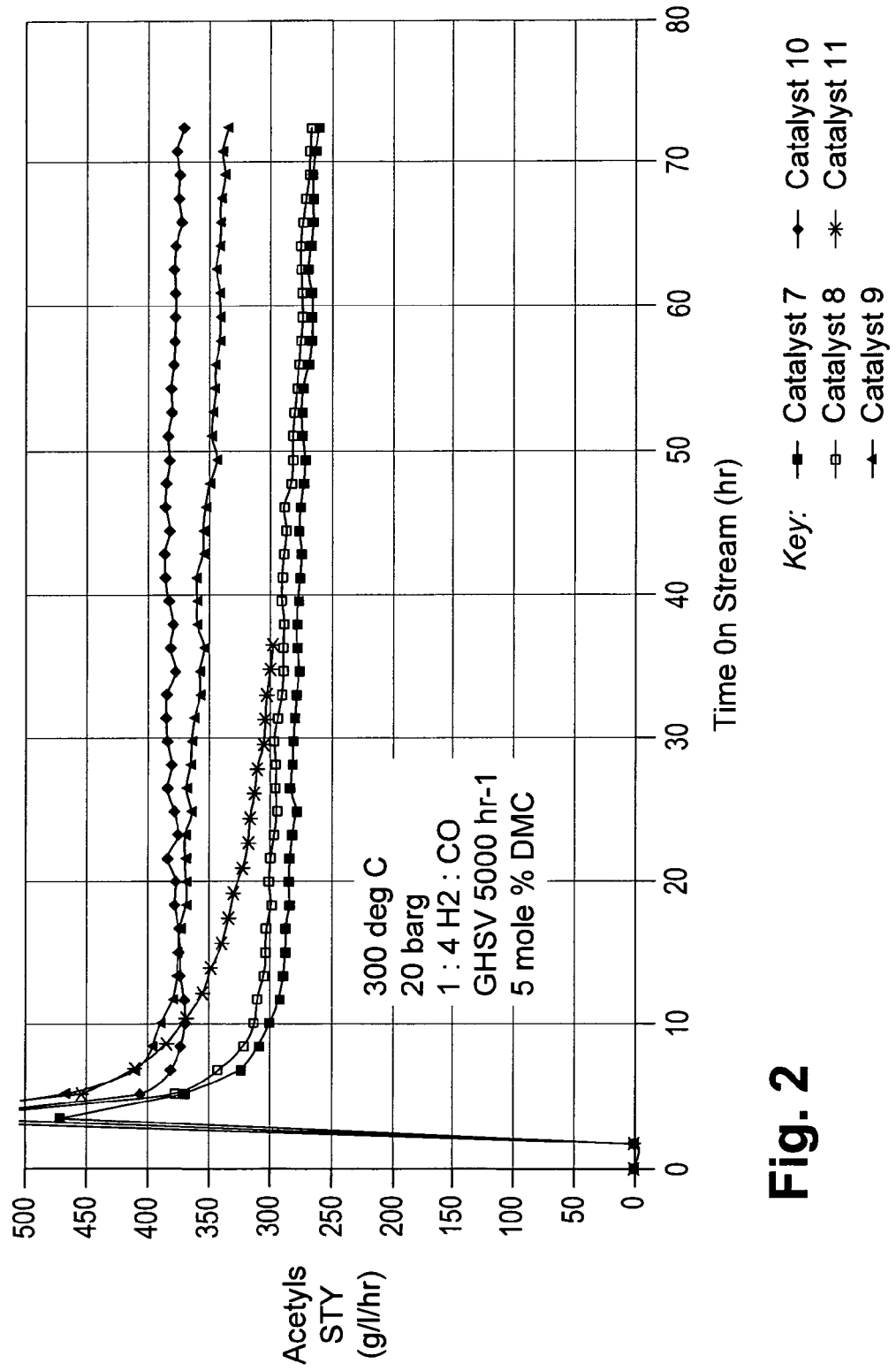
FIG. 2 depicts space time yield (STY) to carbonylation products (g/l/h) versus time on stream (hours) for various composites of copper mordenite with Chinafill 200 binder and a copper mordenite catalyst having no binder.

The results of the carbonylation reactions are shown in FIG. 2

As can be seen from FIG. 2, the catalysts prepared in accordance with the method of the present invention (Catalysts 9 and 10) provide significantly improved STY to carbonylation products compared to the catalysts containing binder but which were not prepared in accordance with the present invention (Catalysts 7 and 8). Catalysts 9 and 10 also provide superior STY to acetyls products compared to the binderless catalyst, Catalyst 11.

EXAMPLE 3

Catalyst Preparation

Catalyst A—Slurry Impregnated Copper Mordenite:Pural SCF Binder 15 g of ammonium mordenite of silica:alumina ratio of 20 (CBV21A, Zeolyst International) and Cu(NO$_3$)$_2$.2.5H$_2$O (2.67 g) were added to deionised water (40 ml) and stirred for 12 hours at room temperature. The solution/suspension was concentrated en vacuo at 80° C. to remove the bulk of the water and then dried at 110° C. for 20 hours to obtain dry copper loaded mordenite. 8 g of the dry copper loaded mordenite was milled to obtain a free flowing powder. The powder and 2 g of Pural SCF binder (ex Sasol) were added to a Büchi powder drying flask and rotated on a rotor evaporator at 100 rpm at ambient temperature and pressure for 1 hour. The contents of the flask were then calcined at 500° C. for 3 hours under an atmosphere of static air to obtain Catalyst A. The copper loading of Catalyst A was 55 mol % relative to aluminium.

Catalyst B—Ion-Exchanged Copper Mordenite:Pural SCF Binder 15 g of ammonium mordenite of silica:alumina ratio of 20 (CBV21A, Zeolyst International) was added to an aqueous solution of Cu(NO$_3$)$_2$.2.5H$_2$O (1.07 g) in deionised water (150 ml) and stirred at 80° C. for 2 hours. The resultant solution/suspension was then filtered and the collected solid washed with copious amounts of deionised water (1.5 liters per 10 g of catalyst). The copper ion-exchanged mordenite was then dried at 110° C. for 20 hours. 8 g of the dried copper loaded mordenite was milled to obtain a free flowing powder. The powder and 2 g of Pural SCF (ex Sasol) were added to a Büchi powder drying flask and rotated on a rotor evaporator at 100 rpm at ambient temperature and pressure for 1 hour. The contents of the flask were then calcined at 500° C. for 3 hours under an atmosphere of static air to obtain Catalyst B. The copper loading of Catalyst B was 55 mol % relative to aluminium.

Catalyst C—Slurry Impregnated Copper Mordenite:Chinafill 200 Binder 20 g of ammonium mordenite of silica:alumina ratio of 20 (CBV21A, Zeolyst International) and Cu(NO$_3$)$_2$.2.5H$_2$O (3.56 g) were added to deionised water (35 ml) and stirred for 15 hours at room temperature. The solution/suspension was concentrated en vacuo at 80° C. to remove the bulk of the water and then dried at 110° C. for 20 hours to obtain dry copper loaded mordenite. 4 g of the dried copper loaded mordenite was milled to obtain a free flowing powder. The powder and 1 g of Chinafill 200 binder (ex Amberge Kaolinwerke) were added to a Büchi powder drying flask and rotated on a rotor evaporator at 100 rpm at ambient temperature and pressure for 1 hour. The contents of the flask were then calcined at 500° C. for 3 hours under an atmosphere of static air to obtain Catalyst C. The copper loading of Catalyst C was 55 mol % relative to aluminium.

Catalyst D—Ion-Exchanged Copper Mordenite:Chinafill 200

4 g of ammonium mordenite of silica:alumina ratio of 20 (CBV21A, Zeolyst International) was added to an aqueous solution of $Cu(NO_3)_2.2.5H_2O$ (0.286 g) in deionised water (40 ml) in an autoclave bomb and stirred at 80° C. for 2 hours. The autoclave bomb was placed in an autoclave oven and rotated rapidly for 2 hours at 80° C. The autoclave bomb was then cooled to ambient temperature. The resultant solution/suspension was filtered through a sinter funnel and the collected solid was washed with copious amounts of deionised water (1.5 liters per 10 g of catalyst). The catalyst was then dried at 110° C. for 20 hours, before being calcined at 500° C. for 3 hours in an atmosphere of static air to obtain Catalyst D. The copper loading of Catalyst D was 55 mol % relative to aluminium.

Carbonylation of Dimethyl Ether

Each of Catalysts A to D was used to catalyse the carbonylation of dimethyl ether with carbon monoxide as follows. Prior to use each of the catalysts was compacted at 10 tonnes in a 13 mm die set using a pneumatic press, and crushed and sieved to a particle size fraction of 125 to 160 microns.

The carbonylation reactions were carried out in a pressure flow reactor unit consisting of 16 identical reactors of the type described in WO 2005063372. Prior to the loading of a catalyst into the reactor, a ca. 5 cm bed of steatite of sieve fraction of 100-350 μm was placed in the respective catalyst holder. A ca. 5 cm zone of corundum of sieve fraction of 125-160 μm was placed on top of the steatite bed. On a dry mass basis (determined by loss on ignition of the relevant catalyst measured by heating the catalyst from room temperature to 600° C. at a ramp rate of ca. 30° C. per minute). 0.625 g of catalyst was then placed on top of the corundum bed. The catalyst was covered by a ca. 5 cm corundum bed of a particle size of 125-160 μm. A ca. 5 cm zone of steatite of sieve fraction of 100-350 μm was placed on top of the corundum bed. Every zone was concreted via hitting or vibrating to get a stable bed and a defined starting height of the catalyst zone. The catalyst was then pressurised to the reaction pressure of 70 bar with $CO/H_2$ 4/1 mixture at a flow rate of 4.0 l/h. The catalyst was then heated at 0.5° C./min to a holding temperature of 220° C., where it was held for 3 hours. The temperature was then ramped to 300° C. at 0.5 deg. C/min, followed by a dwell time of 3 hours. After the dwell time was reached the gas feed was switched to a mixture of carbon monoxide, hydrogen and dimethyl ether with a $CO/H_2$/dimethyl ether ratio of 72/18/10 at a flow rate of 4.275 L/h, with dimethyl ether fed at 0.4275 L/h as a vapour, to obtain a $CO/H_2$/dimethyl ether molar ratio of 72/18/10. In addition, nitrogen gas was introduced at a variable rate of 0-50 ml/min to equalise the pressure swings between the 16 reactor exits. The exit stream from the reactor was passed to a gas chromatograph to determine the concentration of reactants and carbonylation products. The reaction was allowed to continue for 150 hours (148 hours for catalysts C and D) under conditions of 300° C., 70 bar, a gas hourly space velocity (GHSV) of 4275 $h^{-1}$. The carbonylation product was predominantly methyl acetate, with only small amounts of acetic acid being produced. Table 1 shows the results for catalysts A to D after 140 hours.

TABLE 1

| Catalyst | Binder | Binder/ wt. % | Copper mordenite preparation method | Selectivity to MeOAc/% (a) |
|---|---|---|---|---|
| A | Pural SCF | 20 | Slurry Impregnation | 88 |
| B | Pural SCF | 20 | Ion Exchange | 96 |
| C | Chinafill 200 | 20 | Slurry Impregnation | 89 |
| D | Chinafill 200 | 20 | Ion Exchange | 95 |

(a) Selectivity to methyl acetate based upon dimethyl ether converted.

A comparison of catalysts B and D with catalysts A and C respectively, shows that the catalysts, B and D, which were prepared by ion exchange, provide improved selectivity to methyl acetate compared to catalysts A and C, which were prepared by slurry impregnation.

EXAMPLE 4

Catalyst E—Copper Mordenite 20 g of ammonium mordenite of silica:alumina ratio of 20 (CBV21A, Zeolyst International) and $Cu(NO_3)_2.2.5H_2O$ (3.56 g) were added to deionised water (50 mL) and stirred for 12 hours at room temperature. The solution was concentrated in vacuo at 80° C. and then dried at 110° C. for 20 hours, before being calcined at 500° C. for 3 hours in an atmosphere of static air. The mordenite had a copper loading of approximately 55 mole % relative to Al contained in the mordenite.

Catalyst F—Copper Mordenite:Pural SCF 15 g of ammonium mordenite of silica:alumina ratio of 20 (CBV21A, Zeolyst International) and $Cu(NO_3)_2.2.5H_2O$ (2.67 g) were added to deionised water (40 mL) and stirred for 12 hours at room temperature. The solution was concentrated in vacuo at 80° C. and then dried at 110° C. for 20 hours. The mordenite had a copper loading of approximately 55 mole % relative to aluminium contained in the mordenite. 8 g of the dried copper mordenite was gently milled to obtain a free flowing powder. The powder and 2 g of Pural SCF (Sasol) were added to a Büchi powder drying flask and rotated on a rotor evaporator at 100 rpm at ambient temperature and pressure for 1 hour. The contents of the flask were then calcined at 500° C. for 3 hours under an atmosphere of static air.

Carbonylation of Dimethyl Ether

Each of catalysts E and F was used to catalyse the carbonylation of dimethyl ether using the carbonylation method described in Example 3 above. The results after 140 hours reaction time are given in Table 2 below.

TABLE 2

| Catalyst | Binder | Binder/ wt. % | Mordenite catalyst component | Acetyls STY/ g $kg^{-1}$ of mordenite $h^{-1}$ (a) |
|---|---|---|---|---|
| E | None | 0 | Cu-mordenite | 805 |
| F | Pural SCF | 20 | Cu-mordenite | 805 |

(a) STY expressed per kg of mordenite component per hour, excluding the binder component From an inspection of Table 2, it can be seen that the incorporation of binder into a copper loaded mordenite has no detrimental effect on catalytic activity compared to a copper mordenite having no binder.

The invention claimed is:

1. A process for the carbonylation of a carbonylatable reactant selected from at least one of dimethyl ether and methanol, said process comprising carbonylating said carbonylatable reactant with carbon monoxide in the presence of a catalyst to produce a carbonylation product selected from at least one of methyl acetate and acetic acid, which catalyst is formed by compositing a mordenite loaded with at least one of silver and copper, with an inorganic oxide binder.

2. A process according to claim 1 wherein the compositing of the metal loaded mordenite with the binder is carried out by slurry mixing or by dry mixing.

3. A process according to claim 1 wherein the mordenite loaded with at least one of silver and copper is calcined prior to being composited with the binder.

4. A process according to claim 1 wherein the catalyst is calcined.

5. A process according to claim 1 wherein the binder is selected from the group consisting of silicas, aluminas, silica-aluminas, magnesium silicates, magnesium aluminium silicates, titanias, zirconias and clays.

6. A process according to claim 5 wherein the binder is selected from an alumina and a silica-alumina.

7. A process according to claim 1 wherein the binder has a mesoporosity in the range 1 to 500 m2/g as measured by nitrogen BET.

8. A process according to claim 1 wherein the binder has a microporosity in the range 1 to 100 m2/g as measured by nitrogen BET.

9. A process according to claim 1 wherein the binder contains the metals of Group 1 and Group 2 of the Periodic Table of Elements and iron in a total amount in the range greater than 0 to 10 wt %.

10. A process according to claim 1 wherein the binder is present in the catalyst in an amount in the range 10 to 80% by weight of the catalyst.

11. A process according to claim 1 wherein the at least one of copper and silver is loaded onto the mordenite by ion-exchange.

12. A process according to claim 1 in which process there is also present hydrogen.

13. A process according to claim 1 wherein the carbonylatable reactant is dimethyl ether and the process is conducted as an anhydrous process.

14. A process according to claim 1 wherein the carbonylation product comprises methyl acetate and at least some of the methyl acetate is hydrolysed to acetic acid.

* * * * *